United States Patent [19]
Lanzendörfer et al.

[11] Patent Number: 5,952,373
[45] Date of Patent: Sep. 14, 1999

[54] AGENTS ACTING AGAINST HYPERREACTIVE AND HYPOACTIVE, DEFICIENT SKIN CONDITIONS AND MANIFEST DERMATITIDES

[75] Inventors: Ghita Lanzendörfer, Hamburg; Franz Stäb, Echem; Sven Untiedt, Hamburg, all of Germany

[73] Assignee: Beiersdorf AG, Hamburg, Germany

[21] Appl. No.: 08/849,523

[22] PCT Filed: Dec. 12, 1995

[86] PCT No.: PCT/EP95/04907

§ 371 Date: Sep. 8, 1997

§ 102(e) Date: Sep. 8, 1997

[87] PCT Pub. No.: WO96/18381

PCT Pub. Date: Jun. 20, 1996

[30] Foreign Application Priority Data

Dec. 13, 1994 [DE] Germany ................ 44 44 238

[51] Int. Cl.$^6$ ............ A61K 31/35; A61K 31/65
[52] U.S. Cl. ........... 514/456; 514/457; 514/152; 514/858; 514/859; 514/860; 514/861; 514/863; 514/864
[58] Field of Search ............... 514/456, 457, 514/557, 152, 858, 859, 860, 861, 862, 863, 864

[56] References Cited

U.S. PATENT DOCUMENTS 4,297,348  10/1981  Frazier ................. 424/180
5,719,129   2/1998  Andary et al. ........... 514/25

OTHER PUBLICATIONS

*The Merck Index*, 10$^{th}$ Ed., Windholz et al., p. 1315, abstract No. 9021. (1983).

Primary Examiner—Kevin E. Weddington
Attorney, Agent, or Firm—Sprung Kramer Schaefer & Briscoe

[57] ABSTRACT

The invention relates to the use of
   a) a compound or several compounds from the group consisting of flavonoids
   b) of the antioxidants or
   c) of the endogenous energy metabolism metabolites or
   d) of the endogenous enzymatic antioxidant systems and synthetic derivatives thereof (mimics) or
   e) of the antimicrobial action systems or
   f) of the antiviral action systems or
   g) active compounds of the known, conventional treatment forms
in each case for the treatment or prophylactic treatment of hyperreactive skin predisposed to dermatitis or deficient, hypoactive skin or dermatoses.

4 Claims, No Drawings

AGENTS ACTING AGAINST HYPERREACTIVE AND HYPOACTIVE, DEFICIENT SKIN CONDITIONS AND MANIFEST DERMATITIDES

DESCRIPTION

Agents against hyperreactive and hypoactive, deficiency states of the skin and manifest dermatitis.

The present invention particularly relates to active compounds and formulations, in particular for topical use, which are used for prophylaxis and treatment of hyperreactive skin predisposed to dermatitis, and of deficient hypoactive skin and for prophylaxis and treatment of the manifest dermatoses mentioned under I. to XIII., such as, for example, atopic dermatitis, neurodermatitis, atopic eczema and seborrhoeic dermatitis, photoinduced dermatoses (for example Mallorca acne and in particular polymorphic photodermatosis and photodermatitis), rosacea, prurigo forms, pruritus, psoriasis forms, ichthyosis, decubitus, ulcus cruris and microbial and viral infections, such as, for example, herpes simplex, h.zoster or h.labialis.

The skin states according to the invention are explained below in more detail.

Various pathological mechanisms which characterize the clinical picture of hypoactive skin or hyperreactive skin and the dermatoses mentioned under I. to XIII., such as, for example, forms of acne, atopic dermatitis, prurigo forms, psoriasis, photodermatoses, decubitus, ulcus cruris and ichthyosis, are described in the literature. However, the causal pathological mechanisms and the chronology thereof are not sufficiently known for any of the dermatoses mentioned. The treatment methods and active compounds administered which are known to date lead in the most favourable case to a brief improvement in the symptoms. UV treatment and/or chemotherapy (psoralen, PUVA, cyclosporin A, corticosteroids, acyclovir and the like), for example, are used for treatment, with the known adverse side effects on repeated administration.

The object of the invention is to improve this unsatisfactory prior art and to provide cosmetic, dermatological and/or pharmaceutical active compounds and formulations which are used for prophylaxis and treatment of deficient, hypoactive skin or for prophylaxis and treatment of hyperreactive skin with a propensity to dermatitis, and for prophylaxis and treatment of the manifest dermatoses mentioned under sections I. to XIII. below, without inducing the side effects of known agents, even during long-term use.

These objects are achieved according to the invention.

The invention relates to the use of a) a compound or several compounds from the group consisting of flavonoids, or b) an active compound combination comprising a compound or several compounds chosen from the group consisting of flavonoids, in combination with a compound or several compounds chosen from the group consisting of cinnamic acid derivatives, and if appropriate additionally in each case a compound or several compounds from one of the groups or several of the groups c) of the antioxidants or d) of the endogenous energy metabolism metabolites or e) of the endogenous enzymatic antioxidant systems and synthetic derivatives thereof (mimics) or f) of the antimicrobial action systems or g) of the antiviral action systems or h) active compounds of the known, conventional treatment forms in each case for the treatment or prophylactic treatment of hyperreactive skin predisposed to dermatitis or deficient, hypoactive skin or dermatoses.

Active compound combinations b), their use and formulations which comprise these are preferred.

The invention also relates to cosmetic and dermatological formulations, in particular topical formulations and pharmaceutical preparations, having a content of the abovementioned active compounds for treatment and prophylactic treatment of the abovementioned states of the skin or diseases.

The invention also relates to cosmetic and dermatological, in particular topical formulations and pharmaceutical preparations having a content of the abovementioned active compounds according to the invention.

The manifest dermatoses or skin diseases (dermatitis) according to the invention and the most important forms and names thereof are, in particular:

I. Atopic eczema:
  neurodermatitis
  atopic dermatitis, dermatitis atopica
  atopic eczema with type I and type IV contact eczema, aggravated by occupation,
  nappy dermatitis
  milk crust
  eczematous erythroderma II. Contact eczema:
  toxic/irritating contact eczema,
  occupation-related (for example oil/tar; halogens)
  allergic contact eczema, type I or type IV
  photoallergic contact eczema
  contact urticaria
  dyshidrosiform eczema III. Acne:
  acne vulgaris, juvenile and adult (acne with comedones, papulous, pustulous, nodose, i.e. nodular, nodulocystic acne)
  acne conglobata (special form: hidradenitis suppurativa)
  acne fulminans
  acne tetrad
  acne neonatorum
  senile acne (M. Favre-Racouchot)
  mechanical acne forms (excoriated acne)
  acne cosmetica
  folliculitis with superinfected acne (Staphylococci) occupation-related acne forms (for example chlorine acne)

IV. Herpes virus infections:
  herpes simplex (HSV I+II)
  herpes zoster (varicella virus)
  herpes labialis (gingivostomatitis herpetica, mouth-rot, aphthae,
  stomatitis aphthosa,
  paronychia herpetica, eczema herpeticatum aphthoid of posphiscill and Feyrter, vulvovaginitis herpetica, keratoconjunctivitis herpetica, herpes simplex recidivans, herpes genitalis recidivans, herpes glutaelis recidivans, dermatitis herpetiformis)
  varicella virus (herpes zoster, acute posterior ganglionitis, shingles, zona)

V. Bacterial infections:
  non-follicular pyodermas, vulgaris or bullous (impetigo contagiosa, Streptococci, Staphylococci) follicular pyodermas (cocci), furuncles, carbuncles, folliculitis, for example f. barbae
  mycobacterioses (Corynebacteria, Spirochaeta, anaerobic organisms)
  erysipelas (Gram-pos. cocci, Gram-neg. rod-shaped organisms)
  ecthyma forms
  leprosy forms
  erythrasma (*Coryneb. minutissimum*)
  trichomycosis axillaris (*Coryneb. tenuis*)
VI. Psoriasis:
  psoriasis vulgaris
  flaking eczema
  psoriasis pustulosa
  psoriasis arthropatica
  psoriatic erythroderma
VII. Rosacea
VIII. Perioral dermatitis
IX. Prurigo:
  p. simplex acuta (strophulus, urticaria papulosa), subacuta, chronica,
  p.nodularis Hyde
X. Eczema:
  seborrhoeic eczema (p. ovale)
  microbial eczema (nappy dermatitis-Bacillus ammoniagenase, *B. proteus, B. subtilis, E. coli, S. aureus*)
  numular eczema
  dyshidrotic eczema
  desiccating eczema (asteatotic eczema, xerosis, eczema craquele)
  lichen simplex chronicus (neurodermatitis circumscripta)
XI. Photodermatosis:
  radiodermatitis acuta and chronica (UV and ionizing radiation therapy)
  chronic actinic dermatitis
  photourticaria (urticaria solaris)
  polymorphic photodermatosis (other names for polymorphic photodermatosis are PPD, PPE and a large number of other names such as are mentioned in the literature (for example A. Voelckel et al., Zentralblatt Haut- und Geschlechtskrankheiten (1989), 156, page 2))
XII. Decubitus
XIII. Ulcus cruris In the following text, the flavonoids according to the invention are also designated A), the cinnamic acid derivatives are also designated B), the antioxidants are also designated C), the endogenous energy metabolism metabolites are also designated D), the endogenous enzymatic antioxidant systems or substances and synthetic derivatives thereof (mimics) are also designated E), the antimicrobial action systems or active compounds are also designated F), the antiviral action systems for substances are also designated G) and the known conventional treatment forms or substances are also designated H).

Preferred flavonoids according to the invention are, for example, hydroxylated flavones, flavonones, isoflavones or chalcones, and in each case also glycosides thereof, as well as these non-hydroxylated base structures or parent substances.

According to the invention, the flavonoids A) are preferably chosen from the group of substances having the generic structural formulae:

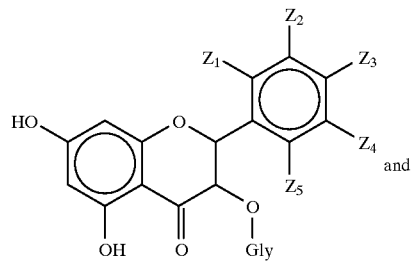

and

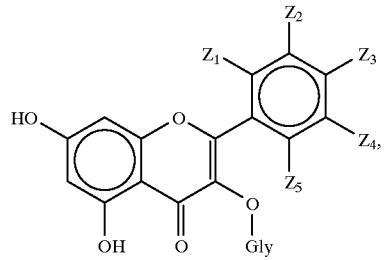

wherein $Z_1$–$Z_5$ independently of one another are chosen from the group consisting of H, OH and O-alkyl, wherein the alkyl groups can be branched and unbranched and can contain 1–18 C atoms, and wherein Gly is chosen from the group consisting of mono- and oligoglycoside radicals, or can also be H. Preferred glycoside radicals are those mentioned below for $Gly_1$–$Gly_3$.

Further flavonoids according to the invention are preferably chosen from the group consisting of substances having the following formulae:

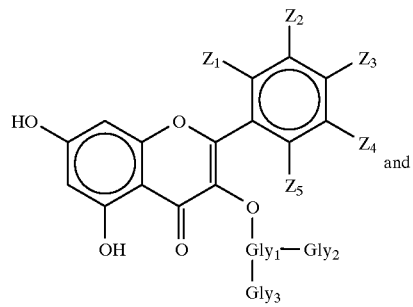

and

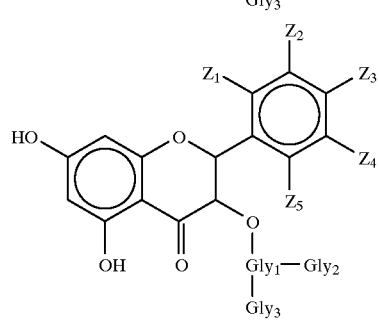

wherein $Z_1$ to $Z_5$ have the abovementioned meaning and $Gly_1$, $Gly_2$ and $Gly_3$ are monoglycoside radicals.

Preferably, $Gly_1$, $Gly_2$ and $Gly_3$ independently of one another are chosen from the group consisting of hexosyl radicals, in particular the rhamnosyl radicals and glucosyl radicals. However, other hexosyl radicals, for example allosyl, altrosyl, apiosyl, arabinosyl, biosidyl, galactosyl, gulosyl, glucoronidyl, iodosyl, mannosyl, talosyl und xylosyl, are also advantageously to be used, where appropriate. It may also be advantageous according to the invention to use pentosyl radicals.

It may likewise be advantageous to dispense with the abovementioned glycosidic radicals $Gly_{1-3}$ and to use the unsubstituted flavonoids ($Gly_{1-3}$=H), such as, for example, quercitin. It may also be of advantage to use flavonoids in which the glucoside radical is bonded to C7, C4', C3' or C5' via phenolic OH functions.

It may moreover be of advantage to use flavonoids in which the phenolic OH function on C9 is present in the free form (so-called chalcones). It is particularly advantageous to use neohesperidin dihydrochalcone from this group.

The invention furthermore relates to compounds of flavonoids or flavone glycosides with derivatives of the abovementioned sugar radicals, such as 1→2; 1→3; 1→4 or 1→5 di-, oligo- or poly-alpha- or -betaglycosidic compounds of the same or different sugars with one another and sugar acids, as well as sugar esters, and also substituted sugars, for example with NR1R2, wherein R1 can be H or alkyl and R2 can be H or alkyl (for example N-acetylglucosamine).

It is advantageous in the context of the present invention to choose the flavone glycoside or glycosides from the group consisting of quercitin, rutin, chrysin, kaempferol, myricetin, rhamnetin, apigenin, luteolin, naringin, hesperidin, naringenin, hesperitin, morin, phloridzin, diosmin, fisetin, vitexin, neohesperidin dihydrochalcone, flavone, glucosylrutin and genistein.

The flavone glucosides which are particularly preferred according to the invention are chrysin, naringin, hesperidin, naringenin, hesperetin, morin, phloridzin, diosmin, neohesperidin dihydrochalcone, flavone and alpha-glucosylrutin of the formula

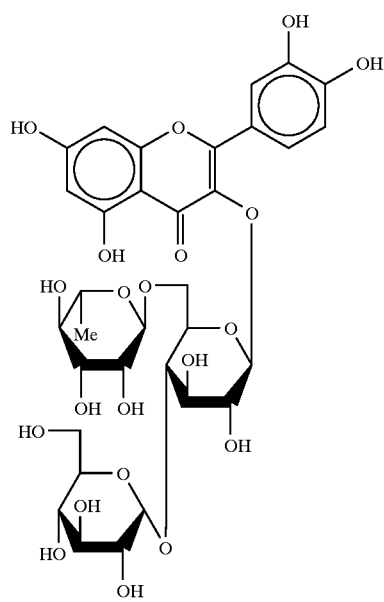

The flavone glucoside which is preferred according to the invention is alpha-glucosylrutin. It is distinguished in particular by the structure shown.

It is particularly advantageous in the context of the present invention to choose the flavone glycoside or glycosides from the group consisting of alpha-glucosylrutin, alpha-glucosylmyrictrin, alpha-glucosylisoquercitrin and alpha-glucosylquercitrin.

Compounds such as alpha-glycosylrutin, alpha-glycosylhesperidin, alpha-glycosylnaringin, alpha-mannosylrutin, alpha-rhamnosylrutin are moreover particularly preferred according to the invention.

It may furthermore be advantageous in the context of the invention to use commercially available flavonoid-containing plant extracts. These can be aqueous-alcoholic or aqueous-glycolic extracts and dry extracts obtained by the customary methods.

The following extracts have proved to be advantageous in particular: citrus fruit peel or kernel extract (for example Citricidal/Synthapharm), soya extract (for example Phytodermin/Chem. Laboratorium Dr. Kurt Richter GmbH), Sophora Japonica extract (for example Sophorine/Solabia), Scotch thistle extract (for example Psoralen Silymarin/Mani GmbH Chemische Produkte), cat's-foot blossom extract, spinach extract and a mixed plant extract of passionflower, blackcurrants and vine leaves (AE Complex/Solabia) and calendula extract (Pot Marigold AMI watersoluble/Alban Muller).

Suitable cinnamic acid derivatives are, for example, hydroxycinnamic acids and derivatives thereof, it being possible for the derivatives to be, for example, those defined below.

Cinnamic acid derivatives of the general formula

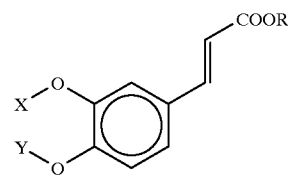

and/or active amounts of cinnamic acid derivatives of the general formula

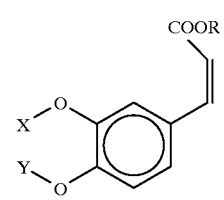

wherein the groups X, Y and R independently of one another can be chosen from the group consisting of H and branched or unbranched alkyl having 1–18 C atoms, can be used according to the invention.

The acids or salts thereof can be used, preferably the physiologically tolerated salts, for example water-soluble salts (sodium and potassium salts).

Ferulic acid is regarded as a particularly advantageous cinnamic acid derivative in the context of the present invention. Ferulic acid (4-hydroxy-3-methoxycinnamic acid, caffeic acid 3-methyl ether) is characterized by the structural formula

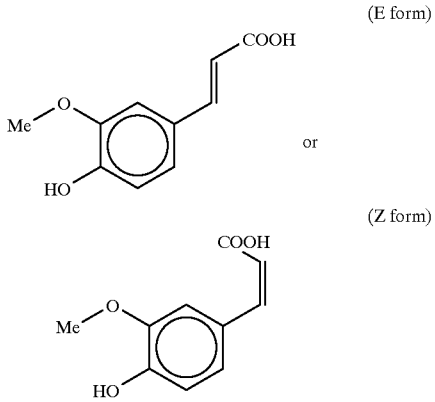

(E form)

or (Z form)

It is widespread in plants and occurs, for example, in beet crops, cereals and the latex of the umbelliferous plants *Ferula asafoetida* and *Ferula nartex* which give it its name. The E form is a colourless crystalline solid under normal conditions, and the Z form is in the form of a yellowish oil under normal conditions.

In the context of the present invention, it is preferable to use E-ferulic acid. However, it is also advantageous, where appropriate, to employ Z-ferulic acid or any desired mixtures of E- and Z-ferulic acid.

Another derivative of cinnamic acid which is preferred according to the invention is caffeic acid, which is distinguished by the structure

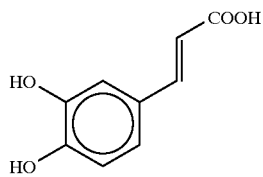

It is a widespread plant acid and is contained, for example, in coffee, tobacco, poppy and dandelion.

It is also advantageous, where appropriate, to use plant extracts with a content of cinnamic acid derivatives according to the invention, in particular ferulic acid and/or caffeic acid.

The term "derivatives of caffeic acid or ferulic acid" is to be understood as meaning their cosmetically or pharmacologically acceptable esters, salts and base adducts, in particular those such as are described above for the cinnamic acid derivatives.

Preferred combinations according to the invention are combinations of one or more substances from the group consisting of the abovementioned flavonoids or combinations consisting of one or more representatives of the flavonoids with a derivative of cinnamic acid, or also the combination with several cinammic acid derivatives.

The combinations of flavonoids, flavone glucosides or flavonoid-containing plant extracts with ferulic acid and the combination of synthetically modified, in particular glycosylated flavonoids, such as alpha-glucosylrutin, with cinnamic acid derivatives are particularly preferred according to the invention.

The weight ratio of the cinnamic acid derivatives to the flavonoid or flavonoids is advantageously 25:1 to 1:25, preferably 5:1 to 1:5, particularly preferably about 2:1 to 1:2.

The cosmetic and dermatological formulations according to the invention preferably comprise 0.001% by weight to 30% by weight, preferably 0.01% by weight to 10% by weight, and in particular 0.1% by weight to 6% by weight, based on the total weight of the formulations, of one or more substances A) according to the invention or of the combination of A) and B).

Formulations with combinations b) which comprise alpha-glucosylrutin and/or ferulic acid are particularly preferred.

The compounds of group A or those of the combination of the active compounds A) and B) can be present in the formulations according to the invention as the sole active compounds.

However, the formulations according to the invention can also additionally have a content of an antioxidant or several antioxidants C), in addition to the active compounds A or the combination of A) and B).

The antioxidants C) according to the invention can advantageously be chosen from the group consisting of tocopherols and derivatives thereof. The tocopherols, also called vitamin E, are derived from the base substance tocol (2-methyl-2-(4,8,12-trimethyltridecyl)chroman-6-ol). The configuration 2R,4'R,8'R is attributed to alpha-tocopherol, which occurs naturally most frequently and is the most important. It is also occasionally called RRR-alpha-tocopherol.

The tocopherol derivatives which are preferred according to the invention are alpha-tocopherol and its esters, in particular alpha-tocopheryl acetate. Esters of acids having 2–18, in particular 2–8 C atoms are preferred.

If vitamin E and/or derivatives thereof are the antioxidant or antioxidants, it is advantageous to choose the particular concentrations thereof from the range from 0.001 to 10% by weight, based on the total weight of the formulation.

Other preferred antioxidants C) according to the invention and antioxidative active compounds are: L-amino acids (for example of glycine, histidine, tyrosine, tryptophan, phenylalanine, methionine, glutamic acid, arginine and serine) and derivatives thereof (for example hydroxyl, methyl and ethyl compounds), imidazoles (for example urocanic acid) and derivatives thereof, peptides having a content of L-histidine, such as, for example, D,L-carnosine, D-carnosine, L-carnosine and derivatives thereof (for example anserine, L-alanylhistidine, L-histidyltryptophan, L-methionylhistidine, L-histidyltyrosyltryptophan and methionyltryptophan) and/or a content of tryptophan (for example L-glycyltryptophan, L-tryptophanylhistidine and L-methionyltryptophan), polyamines (for example spermine and spermidine), carotinoids, carotenes (for example alpha-arotene, β-carotene and lycopin) and derivatives thereof, liponic acid and derivatives thereof (for example dihydroliponic acid), aurothio-glucose, propylthiouracil, oxothiazolidine-4-carboxylate, thiourea and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof, dilauryl thiodipropionate, distearyl thiodipropionate, thiodipropionic acid and derivatives thereof (oxidized and/or reduced forms, esters, ethers, peptides, lipids, nucleotides, nucleosides and salts) and sulfoximine compounds (for example buthionine-sulfoximines, homocysteine-sulfoximine, buthionine-sulfones and penta-, hexa- and heptathionine-sulfoximine) in very low tolerated dosages (for example pmol to mmol/kg). Furthermore (metal)chelators (for example alpha-hydroxy-fatty acids, palmitic acid, phytic acid or lactoferrin), alpha-hydroxy acids (for example citric acid, lactic acid, malic acid, salicylic acid and glyoxylic acid), humic acid, tannic acids, tannins, bile acid and derivatives thereof (for example cholic acid, glucocholic acid, taurocholic acid and taurine), bile extracts, bilirubin, biliverdin, EDTA, EGTA and derivatives thereof, as well as unsaturated fatty acids and derivatives thereof (for example gamma-linoleic acid linoleic acid and oleic acid), folic acid and derivatives thereof, ubiquinone and ubiquinol and derivatives thereof, vitamin C and derivatives (for example ascorbyl palmitate, Mg ascorbyl phosphate, ascorbyl acetates and ascorbyl glycosides), tocotrienols, tocopherols and derivatives thereof (for example vitamin E acetate, alpha-, beta-, gamma- and delta-tocopherols and tocopheryl glycosides), vitamin A and derivatives (retinol, vitamin A palmitate and vitamin A acid) and coniferyl benzoate of benzoin resin, aqueous or alcoholic tobacco, tea and/or coffee extracts, teeine, caffeine, chlorogenic acid, nicotine, nicotinic acid, quercitin, myricitin, ginkgo biloba extracts, Cucumberaceae extracts (for example from cucumbers), brassicaceae extracts (for example from cabbage plants), camomile extract, thyme extract, rosemary extract, kaempferol, benzoic acid and derivatives thereof (for example ethyl, isopropyl and propyl gallate), butylhydroxytoluene, butylhydroxyanisole, nordihydroguaiac resin acid, nordihydroguaiaretic acid, trihydroxybutyrophenone, uric acid, urea and derivatives thereof, mannose, glucose, galactose, fructose and derivatives thereof (for example 6-phosphate, 1,6-diphosphate, dextrans and glucans, in particular beta-glucans), zinc and derivatives thereof (for example ZnO and $ZnSO_4$), selenium and derivatives thereof (for example selenium-methionine), stilbenes and derivatives thereof (for example stilbene oxide and trans-stilbene oxide), calcium and magnesium and derivatives thereof (for example $CaCl_2$ and $MgCl_2$) and the derivatives of these active compounds mentioned which are suitable according to the invention (salts, esters, ethers, alcohols, sugars, nucleotides, nucleosides, peptides and lipids).

The amount of active compound components C) (one or more compounds) in the formulations is preferably 0.001% by weight to 30% by weight, particularly preferably 0.05–20% by weight, in particular 1–10% by weight, based on the total weight of the formulation. According to the invention, these antioxidative active compounds C) can be combined with one or more active compounds of A) and B) and of D) to H) in the concentrations stated there.

Active compounds D) which are preferred according to the invention and favourably influence and regulate energy metabolism and the endogenous, enzymatic antioxidant systems, in particular in the skin, are, for example, vitamin D and derivatives thereof (for example vitamin $D_3$), melatonin and derivatives thereof, D-biotin and derivatives thereof (for example biotin ethyl, methyl, butyl, propionyl and isopropionyl ester and biocytin), glucose and glucose derivatives (for example glucose 6-phosphate, glucose 1,6-phosphate, glucosylcysteine, glucosylcystine, glycosylcysteines, glycosylcystines, glucosylglutathione, glucosylcystamine and glycosylcystamine), pyruvate, coenzyme A and derivatives thereof, coenzyme Q, ubiquinol and derivatives thereof, niacic acids, NADH, NADPH, adenine, adenosine, methyl-S-adenosine, cAMP, ADP, ATP, guanine, guanosine, cGMP, GDP, GTP and $FAD^+$, $FADH_2$, FMN, folic acid, dihydrofolate, riboflavin, pantothenic acid, panthenol, thiaminpyrophosphate, thiamin, 6-phosphoglucurono-delta-lactone, 6-phosphogluconic acid, fructose 6-phosphate, glycerolaldehyde 3-phosphate, ribulose 5-phosphate, pyridoxamine, pyridoxal phosphate, biopterins (for example aminopterin and tetrahydropterin), alpha-hyroxy acids (for example lactic acid), and the suitable derivatives (salts, sugars, esters, ethers, nucleotides, nucleosides, peptides and lipids) of the active compounds mentioned.

The amount of these active compounds D) which regulate energy metabolism is, for example, 0.0001% by weight to 30% by weight, preferably 0.01% by weight to 20% by weight, in particular 0.1% by weight to 10% by weight, in each case based on the total weight of the formulations. These active compounds D) which regulate energy metabolism can be combined according to the invention with active compounds of A) to C) and E) to H) in the concentrations stated there in each case.

Enzymatic antioxidant systems E) which are active according to the invention (for example in formulations in amounts of 0.0001–15% by weight) and synthetic mimics thereof are, for example, the enzyme superoxide dismutase, glutathione peroxidase, glutathione reductase, glutathione S-transferase, oxidoreductases (for example glucose 6-phosphate dehydrogenase, succinate dehydrogenase, malate dehydrogenase, especially $NAD^+$, $NADP^+$ and $FAD^+$ reductases) and carboxylases (for example biotin carboxylase and acetyl-CoA carboxylase), cytochrome P 450 reductase, cytochrome P450 monooxygenases, monoamine oxidase and, in particular, the coenzymes which are active according to the invention (0.0001–5% by weight) and precursors thereof (for example provitamins and vitamins) to the enzymes mentioned.

The amount of enzymatic antioxidants E), which are active according to the invention, in the formulations is preferably 0.001% by weight to 40% by weight, preferably 0.01% by weight to 30% by weight, in particular 0.1% by weight to 15% by weight, based on the total weight of the formulation. The enzymatic antioxidant systems E) which are active according to the invention can be combined according to the invention with one or more active compounds of A) to D) and F) to H) in the concentrations stated there.

Bactericidal and bacteriostatic active compounds F) can be used according to the invention (in particular also in combination with one or more active compounds from A) to E) and G) to H)), such as, for example, vanillic acid, gentian violet, ammonium tumenol, tyrotricin/cetylpyridinium chloride, dequalinium chloride, aluminium chloride, chlorhexidine gluconate, quinolinol, thymol, policresulene, wool wax acids and derivatives thereof, lanthabiotics (such as, for example, nisin), trichlosan, minocycline, doxycycline, tetracycline, omega- and/or alpha-fatty acids (for example $C_5$ to $C_{16}$-chain fatty acids and gamma-linolenic acid and linoleic acid) and esters and alcohols thereof (for example monoglycerol, diclycerol and triglycerol esters and ethyl, methyl, propyl, isopropyl and butyl esters), hamamelis extract, salicylic acid, azelaic acid and derivatives thereof, sulfonamides and antimycotics, such as, for example, imidazole derivatives (for example clotrimazole, econazole, oxiconazole, miconazole, ketoconazole and isoconazole), griseofulvin, terbinafin, nystatin, amphotericin and/or undecylenic acid.

The amount of active antimycotic, bactericidal and/or bacteriostatic active compounds according to the invention in the formulations is preferably 0.0001% by weight to 30% by weight, preferably from 0.001% by weight to 15% by weight, in particular 0.1% by weight to 10% by weight, based on the total weight of the formulation. The bacteriostatic and bactericidal active compounds F) which are active according to the invention can be combined according to the invention with one or more active compounds from A) to D) and G) to H) in the concentrations stated there.

Antiviral active compounds G), such as, for example, aciclovir, famciclovir, gamciclovir and derivatives thereof, can be used according to the invention in combination.

The amount of active antiviral active compounds G) according to the invention in the formulations is preferably 0.0001% by weight to 30% by weight, preferably from 0.001% by weight to 15% by weight, in particular 0.1% by weight to 10% by weight, based on the total weight of the formulation. The antiviral active compounds G) which are active according to the invention can be combined according to the invention with one or more active compounds from A) to F) and from H) in the concentrations stated there.

Known, conventional active systems H), such as, for example, cyclosporin A, cyclophilin, Rapamycin, FK 506, corticoids and derivatives thereof which are active according to the invention, can be used according to the invention in combination.

The amount of the active conventional active compounds H) according to the invention in the formulations is preferably 0.0001% by weight to 30% by weight, preferably from 0.001% by weight to 15% by weight, in particular 0.1% by weight to 10% by weight, based on the total weight of the formulation.

The conventional active compounds H) which are active according to the invention can be combined according to the invention with one or more active compounds from A) to G) in the concentrations stated there in each case.

The following active compounds and active compound combinations with substances from A) to H) are preferred. The amounts by weight stated there are particularly preferred amounts by weight and are based on the total weight of the formulations. The substances are used, including in the formulations according to the invention, for treatment of the abovementioned skin symptoms:

1. Alpha-glycosyl-hesperidin (0.01–15% by weight), ferulic acid (0.001–5% by weight), biocytin (0.001–0.8% by weight), niacic acid (0.001–2.5% by weight), thymol (0.005–2.1% by weight), vitamin E acetate (0.002–12% by weight).
2. Naringin (0.002–10% by weight), ferulic acid (0.001–10% by weight), D-biotin (0.01–0.4% by weight), glucose 6-phosphate (0.001–10% by weight), vitamin E acetate (0.01–15% by weight), L-carnosine (0.05–12% by weight), oleic acid (0.05–0.5% by weight), urea (0.01–12% by weight), dextran (0.001–1% by weight), neohesperidin (0.005–3.0% by weight), pyruvate (0.001–1.5% by weight).
3. Phloridzin (0.001–12% by weight), cystamine (0.01–5.0% by weight), L-histidine (0.01–6% by weight), β-carotene (0.01–3% by weight), ascorbyl palmitate (0.01–8.6% by weight), oleylcysteine (0.01–10% by weight), bile extract (0.02–2.2% by weight), ZnO (0.01–2.0% by weight), folic acid (0.005–2.7% by weight), rutic acid (0.05–6.3% by weight), uric acid (0.02–1.0% by weight), cyclosporin A (0.001–5.0% by weight), ferulic acid (0.001–3.6% by weight), FMN (0.0005–0.25% by weight), wool wax acids (0.005–2.5% by weight).
4. L-Anserine (0.01–3.2% by weight), naringin (0.01–10% by weight), hesperidin (0.01–12% by weight), ferulic acid (0.001–9% by weight), dextran (0.002–10% by weight), butylhydroxyanisole (0.05–0.9% by weight), heptadecanoic acid (0.01–0.9% by weight), N-acetylcysteine (0.01–1.8% by weight), humic acid (0.01–2.7% by weight), ATP (0.004–0.5% by weight), biotin ethyl ester (0.005–0.9% by weight), camomile extract (0.001–6.7% by weight), L-methionine (0.001–2.5% by weight), oxathiazolidine-4-carboxylate (0.001–0.5% by weight).
5. Diosmin (0.01–5.5% by weight), lycopine (0.01–3.8% by weight), L-carnosine (0.01–15% by weight), glycine (0.02–1.2% by weight), liponic acid (0.01–1.8% by weight), folic acid (0.0008–0.5% by weight), palmitic acid (0.01–2.5% by weight), Mg-ascorbyl phosphate (0.002–5.4% by weight), ethyl-cysteine (0.004–4.5% by weight), bilirubin (0.003–1.2% by weight), NADH (0.001–1.6% by weight), mannose (0.01–2.0% by weight), green tea extract (0.01–6.0% by weight), $CaCl_2$ (0.005–5.2% by weight), biocytin (0.005–0.8% by weight), catalase (0.001–1.0% by weight).
6. Cat's-foot blossom extract (0.01–10.0% by weight), ZnO (0.02–1.4% by weight), selenium-methionine (0.01–0.8% by weight), ferulic acid (0.02–4.2% by weight), Sophora Japonica extract (0.01–7.9% by weight), salicylic acid (0.01–3.6% by weight), ubiquinol (0.003–2.8% by weight), vitamin E palmitate (0.02–8.6% by weight), vitamin A oleate (0.02–2.0% by weight), coniferyl benzoate (0.05–1.5% by weight), liposomes (0.02–2.5% by weight), GTP (0.001–0.9% by weight), gamma-linoleic acid from plant oils (0.01–15% by weight), coffee extract (0.01–5.8% by weight), dimethylisosorbitol (0.02–3.4% by weight), $CaCl_2$ (0.005–3.5% by weight), $MgCl_2$ (0.01–2.8% by weight).
7. Cis-urocanic acid (0.005–2.0% by weight), citrus fruit peel extract (0.1–8% by weight), phytic acid (0.01–2.7% by weight), alpha-carotene (0.05–2.9% by weight), thioglucose (0.001–0.9% by weight), ascorbyl glucosides (0.08–5.8% by weight), linoleic acid (0.05–6.4% by weight), lactoferrin (0.002–1.0% by weight), dilauryl thiodipropionate (0.2–2.0% by weight), ubiquinone (0.001–2.1% by weight), $ZnSO_4$ (0.001–2.0% by weight), glutathione (GSSG) (0.004–4.1% by weight), bile acid extract (0.002–2.5% by weight).
8. One or more oxidized and/or reduced thiols (0.001–10% by weight) from the group consisting of the antioxidative active compounds, such as, for example, reduced glutathione (GSH), oxidized glutathione (GSSG), cysteine, N-acetylcysteine, cysteine S-acetate, cystine, oxothiazolidine-4-carboxylate and esters thereof (for example the methyl, ethyl, butyl, propyl, amyl, sorbitosyl, galactosyl, mannosyl, glucosyl, glycosyl, acetyl, lauryl, palmitoyl, oleyl, linoleyl or cholesteryl ester) and salts thereof (for example distearyl thiopropionate or dioleylcysteinyl propionate) in combination with one or more active compounds of the active systems described under 1.–7.
9. Peptide compounds which are active according to the invention (0.001–14% by weight) and/or compounds thereof from the group consisting of antioxidative active compounds, in particular with di- and/or tripeptide compounds which contain the amino acids histidine, tryptophan, tyrosine, methionine or glutamic acid (for example L-alanylhistidine, L-glycylhistidine, L-histidyltryptophan, L-hystidylmethionine or Se-methionylhistidine) and/or polyamines, such as, for example, spermine or spermidine, in combinations with one or more active compounds of the active systems 1–8 mentioned according to the invention.
10. One or more fatty acids and lipid compounds which are active according to the invention (0.0005–12% by weight) and/or compounds thereof from the group consisting of energy metabolism regulators with the active compounds mentioned under 1–9 (for example lauryl, oleyl, linoleyl, palmitoyl, stearyl and cholesteryl or furan compounds) in combinations with one or more of the active systems 1–9 mentioned.
11. One or more nucleic acid derivatives and nucleoside and nucleotide compounds which are active according to the invention (0.0001–7% by weight) and compounds thereof from the group consisting of energy metabolism regulators (for example propylthiouracil, ethylthioadenosine or isopropylguanosylcysteine) in combination with one or more active compounds of the active systems 1–10 mentioned according to the invention.

12. One or more enzymatic antioxidant systems which are active according to the invention (0.0001–5% by weight) and synthetic mimics thereof, such as, for example, the enzymes superoxide dismutase, glutathione peroxidase, glutathione reductase, glutathione S-transferase, oxidoreductases (for example glucose 6-phosphate dehydrogenase, succinate dehydrogenase, malate dehydrogenase, in particular the $NAD^+$, $NADP_+$ and $FAD^+$ reductases) and carboxylases (for example biotin carboxylase or acetyl-CoA carboxylase), cytochrome P 450 reductase, cytochrome P450 monooxygenases or monoamine oxidase in combinations with one or more active compounds of the active systems mentioned under 1–11.

13. One or more coenzymes which are active according to the invention (0.0001–5% by weight) and precursors thereof (for example provitamins and vitamins), such as, for example, biocytin, D-biotin and derivatives thereof (biotinethyl, methyl, butyl, propionyl or isopropionyl ester or biocytin), glucose and glucose derivatives (for example glucose 6-phosphate, glucose 1,6-phosphate, glucosylcysteine, glucosylcystine, dextrans, glycosylcysteines, glycosylcystines, glucosylglutathione, glucosylcystamine or glycosylcystamine), pyruvate, coenzyme A and derivatives thereof, niacic acid, NADH, NADPH, adenine, adenosine, methyl S-adenosine, AMP, cAMP, ADP, ATP, guanine, guanosine, GMP, cGMP, GDP, GTP and $FAD^+$, $FADH_2$, FMN, folic acid, dihydrofolate, riboflavin, pantothenic acid, panthenol, thiamin pyrophosphate, thiamin, 6-phosphoglucurono-delta-lactone, 6-phosphogluconic acid, fructose 6-phosphate, glycerylaldehyde 3-phosphate, ribulose 5-phosphate, pyridoxamine, pyridoxal phosphate, biopterins (for example aminopterin or tetrahydropterin), coenzyme Q and derivatives thereof (for example ubiquinol), vitamin D and derivatives thereof (for example vitamin $D_3$) and the suitable derivatives (salts, sugars, esters, alcohols, ethers, nucleotides, nucleosides, peptides and lipids) in combinations with one or more active compounds of the active systems mentioned under 1–12.

14. Flavonoids, for example alpha-glycosylrutin and/or hesperidin and/or naringin, as an individual substance or in combinations with one or more compounds of the active systems mentioned under 1–13.

15. Flavonoids in combination with cinnamic acid derivatives, for example ferulic acid and/or caffeic acid, in combination with one or more active compounds of the active systems mentioned under 1–14.

These individual components in the particular active systems 1–15 and the concentration data thereof are mentioned by way of example without the intention being to exclude the use of other active compounds mentioned and derivatives thereof or combinations and concentrations thereof which are active according to the invention.

It has furthermore proved to be advantageous in the prophylaxis and treatment of the dermatoses and hyperreactive and/or hypoactive deficiency states of the skin mentioned according to the invention under I. to XIII. to combine the active compounds according to the invention, and in particular the active compound systems 1–15, with urea and/or arginine (for example 0.01–15% by weight). The use of urea in cosmetic and dermatological formulations for treatment, in particular of dry states of the skin, is general prior art.

The term hypoactive states of the skin is to be understood according to the invention as meaning degenerative states of the skin which result in hypofunctioning of the skin and the integumentary appendages. This hypofunctioning can have its causes at the molecular level and be intra- or extracellular, such as, for example, hypofunctioning of the glutathione redox system, of catalase, of superoxide dismutase or of pyruvate carboxylase. As a consequence, the intra- and extracellular antioxidant status or energy metabolism status of individual cells, for example of the fibroblasts in the dermis or of the keratinocytes and Langerhans' cells in the epidermis, or even of the entire skin would be hypoactive.

The term hyperactive states of the skin is to be understood according to the invention as meaning states of the skin in which hyperexpression beyond the normal level, for example of individual metabolic routes or enzyme activities, such as, for example, phosphodiesterase activity, monoamine oxygenase activity or transaminase activity, is present. As a consequence, hyperproliferation, for example of the keratinocytes, or hyperactivity of Langerhans' cells or T-lymphocytes can be found.

The manifest dermatitis mentioned according to the invention means the dermatitis mentioned under I. to XIII. and their manifestations and synonyms.

It has also proved to be advantageous to use the active compounds and active compound combinations A) to E) for prophylaxis and treatment of the dermatitis mentioned according to the invention under I. to XIII. and for the hypo- and hyperactive states of the skin.

For treatment and prophylaxis of the microbially associated dermatitis, such as, for example, atopic eczema, psoriasis and acne forms, seborrhoeic eczema, ichthyosis and bacterial infections and mycoses, such as, for example, in the case of nappy dermatitis, it has proved to be advantageous to combine the active compounds and active compound combinations A) to E) and H) according to the invention with the antimicrobial active systems F).

For treatment and prophylaxis of virally associated dermatitis, such as, for example, the herpes infections mentioned according to the invention under IV:, it has proved to be advantageous to combine the active compounds and active compound combinations A) to E) and H) according to the invention with the antimicrobial active systems G). For viral and microbial superinfections, it has proved to be particularly advantageous also to add a combination of active compounds from F) and G) to the active compound combinations of A) to D) and H) chosen.

For prophylaxis and treatment of hypo- and hyperactive states of the skin and the dermatoses and deficiency states of the skin mentioned according to the invention, it is particularly advantageous to use the following combinations A–G, which, in particular, for: atopic dermatitis, can be composed, for example, of the following individual substances and derivatives thereof: Combination A: alpha-glycosylrutin 0.4% by weight, hesperidin 0.1% by weight, L-carnosine 0.4% by weight, D-biotin 0.05% by weight, vitamin A palmitate 0.8% by weight, vitamin E acetate 1.5% by weight, wool wax acids 0.2% by weight, citric acid 1.0% by weight, glucosylcystamine, 0.04% by weight, oleic acid 0.3% by weight, adenosine 0.8% by weight, ferulic acid 1.2% by weight, ubiquinone 0.5% by weight, vanillic acid 0.2% by weight.

Combinations of this active compound composition with the abovementioned active systems 1–4, 7–9, 12 and 13 have also proved to be particularly advantageous for these dermatoses.

The combination of the above individual active compounds according to the invention and the active systems mentioned under 1–13 and A–F with urea has also proved to be advantageous.

The following combination B, which can be composed, for example, of the following individual substances and derivatives thereof, is furthermore preferred, for example, in particular for psoriasis: Combination B: alpha-glycosylnaringin 2.8% by weight, carnosine 1.0% by weight, methyl-S-adenosine 1.5% by weight, ferulic acid 0.4% by weight, alpha-hydroxypalmitic acid 0.2% by weight, oleic acid 0.3% by weight, cysteine S-acetate 0.05% by weight, vitamin E acetate 3.0% by weight, vitamin A palmitate 1.0% by weight, deoxycholate 0.04% by weight.

Treatment with these active compounds in combination with active systems 2–5, 7, 8, 10 and 13 has also proved to be particularly advantageous for psoriasis forms.

The following combination C, for example, which can be composed of the following individual substances and derivatives thereof, is furthermore preferred, in particular for prurigo forms and pruritus forms: Combination C: phloridzin 1.8% by weight, ferulic acid 0.8% by weight, diosmin 0.2% by weight, 0.8% by weight, citric acid 1.4% by weight, glutamylcysteine 0.05% by weight, glutamic acid 0.5% by weight, L-arginine 1.0% by weight, vitamin E palmitate 1.5% by weight, liponic acid 0.005% by weight, L-carnosine 1.8% by weight, sylimarin 0.3% by weight.

These active compounds in combination with active systems 2–4, 6, 7, 9, 12 and 13 have also proved to be particularly advantageous for treatment of prurigo forms and pruritus forms.

The following combination D, for example, which can be composed of the following individual substances and derivatives thereof, is furthermore preferred, in particular for photodermatoses, above all polymorphic photodermatosis: Combination D: glycosylhesperidin 2.0% by weight, alpha-glycosylrutin 0.3% by weight, ferulic acid 1.2% by weight, D,L-carnosine 0.7% by weight, L-tyrosine 0.2% by weight, methionine 0.9% by weight, vitamin E acetate 2.0% by weight, mannose 0.5% by weight, malic acid 1.0% by weight, oleic acid 0.3% by weight, uric acid 0.05% by weight, cysteine S-acetate 0.8% by weight, ascorbyl palmitase 1.5% by weight.

Combinations of these active compounds with active systems 3, 5–9 and 12 have also proved to be particularly advantageous for prophylaxis and treatment of photodermatoses, in particular polymorphic photodermatosis.

Combination E, which can be composed of the following individual substances and derivatives thereof, is furthermore preferred, in particular for prophylaxis and treatment of acne forms:
Combination E: naringinin 2.8% by weight, Z-ferulic acid 1.2% by weight, vanillic acid 0.3% by weight, methionine 0.6% by weight, L-serine 0.9% by weight, D-biotin 0.02% by weight, citric acid 0.5% by weight, lactic acid 0.4% by weight, malic acid 0.3% by weight, caffeic acid 0.9% by weight, glutamic acid 0.5% by weight, pantothenic acid 0.6% by weight, vitamin E nicotinate 0.5% by weight, salicylic acid 0.8% by weight, tannic acid 0.3% by weight, thiamin 0.3% by weight, oleic acid 0.3% by weight.

Combinations of these active compounds with active systems 3, 6, 7, 9, 12 and 13 have also proved to be particularly advantageous for prophylaxis and treatment.

Combination F, which can be composed, for example, of the following individual substances, has proved to be particularly suitable for prophylaxis and treatment of the viral infections mentioned, in particular herpes infections of the mucosae:

Combination F: glucosyl-naringin 2.0% by weight, E-ferulic acid 0.5% by weight, biocytin 0.15% by weight, L-methionine 1.1% by weight, niacic acid 0.3% by weight, tannic acid 0.4% by weight, citric acid 0.4% by weight, AE-Complex/Solabia 1.5% by weight, β-glucan 1.5% by weight, soya extract 0.3% by weight.

Combinations of these active compounds with active systems 1 and 4–12 have also proved to be particularly advantageous for prophylaxis and treatment of viral infections.

Combination G, which can comprise the following individual substances, has proved to be particularly suitable for prophylaxis and treatment of wounds, in particular chronic wounds, such as, for example, ulcus cruris or decubitus.

Combination G: naringinin 0.6% by weight, diosmin 0.5% by weight, alpha-glycosylhesperitin 0.8% by weight, ferulic acid 0.2% by weight, biotin 0.05% by weight, citric acid 0.4% by weight, dextran (molecular weight 10,000–5 million) 2% by weight, folic acid 0.2% by weight, niacic acid 0.4% by weight, cat's-foot blossom extract 0.5% by weight.

Combinations of these active compounds with active systems 1 and 4–13 have also proved to be particularly advantageous for prophylaxis and treatment, in particular of chronic wounds.

These individual components and the concentrations thereof in a formulation are mentioned by way of example without thereby excluding the use of other antioxidants and active compounds.

In the above combinations A to G, the % by weight data stated are in each case based on the total weight of the formulations or, for example, of the formulations of the examples. These combinations A to G are used in the examples.

For prophylaxis, the active compounds are administered to reduce the frequency and severity of manifestations of the diseases. Treatment in the manifest stage leads to a shortening thereof and to an alleviation of the symptoms.

Treatment with the active compounds according to the invention also serves to prevent or alleviate side effects and secondary damage which may occur when conventional treatment forms are used, such as, for example, UV treatment of psoriasis forms (PUVA treatment) and of atopic eczema and photodermatoses.

The active systems according to the invention, as an accompanying treatment form, furthermore allow a reduction in the dosage of conventional pharmacological active compounds, such as, for example, corticoids, for inflammatory dermatoses.

It is furthermore advantageous also to use the active compounds and formulations according to the invention in combination with conventional active compounds and methods usually used for treatment of the dermatoses mentioned (for example cyclosporin A, corticosteroids, psoralen, UV treatment, PUVA treatment, UVA and/or UVB filters, urea, antibiotics and aciclovir).

The active compounds according to the invention and combinations thereof and the formulations obtained with them, such as pharmaceutical preparations and topical formulations in the form of creams, lotions, gels and sprays, as well as solutions (for example aqueous, alcoholic or aqueous-alcoholic) and other suitable formulations are prophylactically active, in particular, in that they protect sensitive skin predisposed to the dermatoses mentioned under I. to XIII., in particular in the case of atopic dermatitis and photodermatoses, or reduce the development of these. For this, the formulations comprising the active compounds are used regularly once and several times daily. In the case of the manifest dermatoses mentioned, in particular atopic dermatitis (for example atopic eczema or neurodermatitis), ichthyosis, polymorphic photodermatosis, psoriasis and pruritus, an improvement in the state of the skin, in particular a subsidence in the itching which occurs with these dermatoses, takes place after adequate treatment with the active compounds and formulations according to the invention. The diseases can then be further treated prophylactically.

It was surprising and also not to be foreseen by the expert that the active compounds and formulations according to the invention can be used, in particular after topical application to human skin, for prophylaxis and treatment of the dermatoses mentioned under I. to XIII. and of sensitive, hyperreactive skin predisposed to dermatitis, and the combinations according to the invention of flavone glycosides and cinnamic acid derivatives and/or with antioxidant systems and/or active compounds which regulate endogenous energy metabolism, in particular in the skin, and/or antimicrobial active principles can achieve a synergistic action.

The action mechanism of the new active compounds and formulations according to the invention has not yet been clarified completely. It is assumed that an increased, oxidative, free-radical stress exists as the cause of the deficiency or pathological states of the skin in question, this being alleviated or even regulated to the normal level of intact and healthy skin by treatment with the active compounds according to the invention. It is also advantageous that the active compounds employed according to the invention also assist the enzymatic antioxidant and repair systems and the endogenous energy metabolism of the skin, so that an additive or even synergistic action mechanism exists in the active systems and formulations used according to the invention. These active compounds can arise at the site of action on the surface of the skin, mucous membrane and/or integumentary appendages, or by penetration via the sebaceous and sweat glands, and also along hair shafts or through the stratum corneum. For this, on the one hand certain active compounds according to the invention (for example antimicrobial active compounds) can be prevented from penetration into the skin in the formulations according to the invention, for example by coupling to specific carriers, so that only a superficial action is achieved on the skin and/or the hair and/or in the sebaceous and/or sweat glands and/or the hair shafts. To improve the penetration of certain active compounds into the skin, on the other hand, penetration promoters, such as, for example, dimethyl sulphoxide, azones, unsaturated fatty acids (for example oleic acid or cis-alkene fatty acids), heptadecanoic acid, liposomes, nanosomes, microsomes, niosomes and other encapsulation forms, can be added, or the active compounds can be packaged in these in order to achieve a sustained release and/or preserving effect.

Antimicrobial and/or antiviral active principles in combination with the antioxidant systems according to the invention and/or the systems which regulate endogenous energy metabolism can furthermore be used, in particular, for prophylaxis and treatment of dermatitis, such as, for example, neurodermatitis, atopic eczema, seborrhoeic eczema, rosacea, ichthyosis, and acne and psoriasis forms, and of viral infections, such as, for example, herpes simplex, h. labialis and h. zoster.

Such active systems or formulations should furthermore comprise active compounds which can be used for immunohomeostasis of diseased skin, and advantageously here also for immunostimulation in the sense of the action which promotes wound healing, especially with decubitus and ulcus cruris.

The active compounds according to the invention are particularly advantageously chosen from the group consisting of flavonoids and their glucosides, from the group consisting of cinnamic acid derivatives, in particular from the group consisting of ferulic acid derivatives and caffeic acid derivatives, and from the group consisting of antioxidants, in particular the group consisting of tocopherols and their derivatives and imidazoles and derivatives thereof.

Japanese Laid-Open Specification Hei-06-138,941 indeed describes oral formulations having a content of water-soluble glucosides, which can be chosen, for example, from the group consisting of α-glucosylrutin, α-glucosylmyrictrin, α-glucosylisoquercitrin and α-glucosylquercitrin. Japanese Laid-Open Specification Hei-04-363,395 describes a process for preventing decomposition of perfume constituents which is distinguished, inter alia, by an addition of α-glucosylrutin to the corresponding formulations. European Laid-Open Specification 586 303 and European Laid-Open Specification 595 694 furthermore describe the use of flavonoids as antioxidants or light protection substances in cosmetics. It is furthermore known from U.S. Pat. Nos. 4,144,325 and 4,248,861 and from numerous other documents to employ vitamin E in cosmetic and dermatological light protection formulations. The use according to the invention of vitamin E and its derivatives in the combinations according to the invention for cosmetic or dermatological prophylaxis and/or treatment of the dermatoses mentioned and of hyper- and hypoactive states of the skin, however, was not made obvious by the prior art.

No indication which could lead in the direction of the present direction is to be found in these specifications.

If vitamin E and/or derivatives thereof are the antioxidant or antioxidants, it is advantageous to choose the particular concentrations thereof from the range from 0.001 to 10% by weight, based on the total weight of the formulation.

The cosmetic and/or dermatological formulations according to the invention can have the customary composition and can be used for prophylaxis and/or treatment of the skin in the context of dermatological treatment or prophylaxis and/or treatment in the context of cosmetics. They preferably comprise 0.01% by weight to 20% by weight, but in particular 0.1% by weight to 6% by weight, based on the total weight, of one or more active compounds according to the invention.

It is advantageous according to the invention to use combinations of several of the active compounds according to the invention, especially if at least one of the components chosen from the group consisting of flavonoids or glucosides thereof and cinnamic acid derivatives is selected.

It is particularly advantageous to use combinations of flavonoids or derivatives thereof, cinnamic acid and its derivatives and antioxidants, in particular vitamin E and its derivatives.

For the preferred use, the active systems or formulations according to the invention comprising such active compounds, preferably combinations of flavonoids or derivatives thereof, cinnamic acid and derivatives thereof and antioxidants, in particular vitamin E and derivatives thereof, in combination with energy metabolism metabolites and/or antimicrobial active systems, are applied to the skin in an adequate amount in the manner customary for cosmetics or dermatological agents.

The cosmetic and dermatological formulations according to the invention can be in various forms. They can thus be, for example, a solution, an emulsion of the water-in-oil (w/o) type or of the oil-in-water (o/w) type, or a multiple emulsion, for example of the water-in-oil-in-water (w/o/w) or oil-in-water-in-oil (o/w/o) type, a gel, a solid stick or also an aerosol. They are prepared in a manner known per se.

The cosmetic and dermatological formulations according to the invention can comprise cosmetic and dermatological auxiliaries such as are usually used in such formulations, for example UV/A and UV/B filters, preservatives, bactericides, perfumes, agents for preventing foaming, dyestuffs, pigments which have a colouring action, thickeners, surface-active substances, emulsifiers, softening substances, humidifying and/or humectant substances, fats, oils, waxes or other customary constituents of a cosmetic formulation, such as alcohols, polyols, polymers, foam stabilizers, electrolytes, organic solvents or silicone derivatives.

It is also advantageous to administer the active compound combinations according to the invention in encapsulated form, for example encapsulated in collagen matrices and other customary encapsulating materials, for example as cellulose encapsulations, in gelatin or wax matrices or liposomally. Wax matrices such as are described in DE-A-43 08 282 have proved to be particularly favourable.

If the cosmetic or dermatological formulation is a solution or lotion, solvents which can be used are:

water or aqueous solutions;

oils, such as triglycerides of capric or of caprylic acid, or liquid triglycerides of natural origin;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

silicone oils, such as dimethylpolysiloxanes, diethylpolysiloxanes, diphenylpolysiloxanes and mixed forms thereof;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutylether, diethylene glycol monomethyl or monoethyl ether and analogous products.

Mixtures of the abovementioned solvents are used in particular. In the case of alcoholic solvents, water can be a further constituent.

Emulsions according to the invention, for example in the form of a sunscreen cream or sunscreen lotion or a sunscreen milk, are advantageous and comprise, for example, the fats, oils, waxes and other fatty substances mentioned, as well as water and an emulsifier such as is usually used for such a type of formulation.

Gels according to the invention usually comprise alcohols of low C number, for example ethanol, isopropanol, 1,2-propanediol, glycerol and water, or an abovementioned oil, in the presence of a thickener, which is preferably silicon dioxide or an aluminium silicate in the case of oily-alcoholic gels and is preferably a polyacrylate in the case of aqueous-alcoholic or alcoholic gels.

Anhydrous cosmetic and dermatological formulations, such as ointments or skin oils, according to the invention are advantageous and comprise, for example, the fats, oils, silicone oils, waxes and other fatty substances mentioned.

Solid sticks according to the invention comprise, for example, naturally occurring or synthetic waxes, fatty alcohols or fatty acid esters. Lip care sticks are preferred.

Suitable propellants for cosmetic or dermatological formulations according to the invention which can be sprayed from aerosol containers are the customary known readily volatile, liquefied propellants, for example hydrocarbons (propane, butane, isobutane), which can be employed by themselves or as a mixture with one another. Compressed air can also advantageously be used.

The expert of course knows that there are propellent gases which are non-toxic per se which would be suitable in principle for the present invention, but which should nevertheless be omitted because of an unacceptable action on the environment or other concomitant circumstances, in particular fluorohydrocarbons and fluorochlorohydrocarbons (CFCs).

The formulations according to the invention can furthermore preferably comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulation, in order to provide cosmetic formulations which protect the skin from the entire range of ultraviolet radiation. They can also be used as sunscreen agents.

The UVB filters can be oil-soluble or water-soluble. Oil-soluble substances which may be mentioned are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di-(2-ethylhexyl) 4-methoxybenzalmalonate;

2,4,6-trianilino-(p-carbo-2'-ethyl-1'-hexyloxy)-1,3,5-triazine.

Water-soluble substances which may be mentioned are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and its salts.

The list of UVB filters mentioned, which can be used in combination with the free radical scavengers according to the invention, is of course not intended to be limiting.

The invention also relates to the combination of one or more active compounds according to the invention with one or more UVB filters, and cosmetic or dermatological formulations according to the invention which also comprise one or more UVB filters.

It may also be advantageous to combine one or more active compounds according to the invention with UVA filters which have usually been contained to date in cosmetic and/or dermatological formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations and formulations which comprise these combinations. The amounts used for the UVB combination can be employed.

Advantageous formulations are furthermore obtained if the active compounds according to the invention are combined with UVA and UVB filters.

Cosmetic formulations comprising free radical collectors according to the invention can also comprise inorganic pigments which are usually used in cosmetics for protecting the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide.

The invention also relates to these combinations of UVA filters and/or UVB filters and pigment and to formulations which comprise this combination. The amounts mentioned for the above combinations can be used.

The use of active compound combinations according to the invention for protection of the skin and/or hair against exposure to oxidation, in particular this use of the active compound combinations according to the invention in shampoos and washing formulations, is therefore also regarded as an advantageous embodiment of the present invention. Cosmetic formulations which are a skin cleansing composition or shampooing composition preferably comprise at least one anionic, nonionic or amphoteric surface-active substance or also mixtures of such substances, active compounds according to the invention and auxiliaries such as are usually used for this purpose. The surface-active substance or the mixtures of these substances can be present in the shampooing composition in a concentration of between 1% by weight and 50% by weight.

If the cosmetic or dermatological formulations are in the form of a lotion which is rinsed out and is used, for example, before or after bleaching, before or after shampooing, between two shampooing steps or before or after permanent wave treatment, they are, for example, aqueous or aqueous-alcoholic solutions which comprise, if appropriate, surface-active substances, preferably nonionic or cationic surface-active substances, the concentration of which can be between 0.1 and 10% by weight, preferably between 0.2 and 5% by weight. These cosmetic or dermatological formulations can also be aerosols with the auxiliaries usually used for this purpose.

Formulations for treatment of the scalp and hair can be in the form of emulsions which are of the nonionic or anionic type. Nonionic emulsions comprise, in addition to water, oils or fatty alcohols, which can also be polyethoxylated or polypropoxylated, for example, or also mixtures of the two organic components. If appropriate, these emulsions comprise cationic surface-active substances.

According to the invention, cosmetic formulations for treatment of the skin, scalp and hair can be in the form of gels or hair lotions which comprise, in addition to an active content of active compounds according to the invention and solvents usually used for this purpose, preferably water, also organic thickeners, for example gum arabic, xanthan gum, sodium alginate, cellulose derivatives, preferably methylcellulose, hydroxymethylcellulose, hydroxyethylcellulose, hydroxypropylcellulose or hydroxypropylmethylcellulose, or inorganic thickeners, for example aluminium silicates, such as, for example, bentonites, or a mixture of polyethylene glycol and polyethylene glycol stearate or distearate. The gel comprises the thickener, for example, in an amount of between 0.1 and 30% by weight, preferably between 0.5 and 15% by weight.

Unless stated otherwise, all the amounts data, contents and percentage contents are based on the weight and the total weight or on the total weight of the formulations.

Pharmaceutical preparations, agents or compositions which comprise the compounds according to the invention or derivatives or pharmaceutically tolerated salts thereof together with a pharmaceutically tolerated diluent or carrier are also provided according to the invention as formulations.

The compounds of the present invention can be used on humans orally or parenterally, for example in a dosage of 0.01 to 5000 mg, preferably 1 to 500 mg per day, in particular also in subdivided doses, for example twice to four times daily.

The active compounds according to the invention can be mixed with customary pharmaceutically tolerated diluents or carriers and, if appropriate, with other auxiliaries, and can be administered, for example, orally or parenterally. They can preferably be administered orally in the form of granules, capsules, pills, tablets, film-coated tablets, sugar-coated tablets, syrups, emulsions, suspensions, dispersions, aerosols and solutions and liquids, or else as suppositories or vaginal beads, or parenterally, for example in the form of solutions, emulsions or suspensions. Preparations to be administered orally can comprise one or more additives, such as sweeteners, flavourings, dyestuffs and preservatives. Tablets can comprise the active compound mixed with customary pharmaceutically tolerated auxiliaries, for example inert diluents, such as calcium carbonate, sodium carbonate, lactose and talc, granulating agents and agents which promote disintegration of the tablets on oral administration, such as starch or alginic acid, binders, such as starch or gelatin, and lubricants, such as magnesium stearate, stearic acid and talc.

Suitable carriers are, for example, milk sugar (lactose), gelatin, maize starch, stearic acid, ethanol, propylene glycol, ethers of tetrahydrofurfuryl alcohol and water.

The formulations are prepared, for example, by extending the active compounds with solvents and/or carriers, if appropriate using emulsifying agents and/or dispersing agents, it being possible, for example in the case where water is used as a diluent, for organic solvents to be used as auxiliary solvents if appropriate.

Administration is effected in the customary manner, preferably orally or parenterally, in particular perlingually or intravenously. In the case of oral use, tablets can of course also contain, in addition to the carriers mentioned, additives, such as sodium citrate, calcium carbonate and dicalcium phosphate, together with various additives, such as starch, preferably potato starch, gelatin and the like. Lubricants, such as magnesium stearate, sodium lauryl sulphate and talc, can furthermore be co-used for tablet-making. In the case of aqueous suspensions and/or elixirs intended for oral uses, various flavour improvers or dyestuffs, in addition to the abovementioned auxiliaries, can be added to the active compounds.

In the case of parenteral use, solutions of active compounds can be employed, using suitable liquid carrier materials.

Capsules can comprise the active compound as the sole constituent or as a mixture with a solid diluent, such as calcium carbonate, calcium phosphate or kaolin. The injectable preparations are likewise formulated in a manner known per se.

The pharmaceutical preparations can comprise the active compound in an amount of 0.1 to 90% by weight, in particular 1–90% by weight. Capsules are particularly preferred. Individual doses preferably comprise the active compounds in an amount of 0.01 mg–500 mg.

The invention also relates to pharmaceutical and topical formulations, which are characterized in that they comprise a combination of antioxidants and regulating active compounds according to the invention, and the combination of antioxidants and/or regulating active compounds according to the invention with antiviral and/or antimicrobial active principles as described above.

Unless stated otherwise, all the amounts data, contents and percentage contents are based on the weight and the total amount or on the total weight of the formulations.

In the examples, the combinations A–G of individual substances mentioned are used with the parts by weight stated, which in each case represent the weight ratios of the individual substances in the formulation.

The following examples are intended to illustrate the present invention.

EXAMPLE 1
Aqueous formulation (facial lotion)

|  | % by weight |
|---|---|
| PEG 40-hydrogenated castor oil | 0.811 |
| Dipropylene glycol | 2.534 |
| PEG-8 | 1.521 |
| $Na_3EDTA$ | 0.253 |
| Polymer JR 125 | 0.025 |
| Vitamin E acetate | 4.0 |
| Combination E |  |
| Vitamin C palmitate | 1.0 |
| Vitamin E nicotinate | 0.5 |
| Water, completely desalinated | to 100.000 |

EXAMPLE 2
Aqueous composition

|  | % by weight |
|---|---|
| Poly-fatty acid ester (Cetiol HE) | 16.000 |
| PPG 3-myristyl ether (Witconol APM) | 1.000 |
| Propylene glycol | 3.000 |
| Glycerol | 24.000 |
| Alpha-glycosylrutin | 1.6 |
| L-Cystine | 3.8 |
| Heptadecanoic acid | 0.1 |
| L-Alanylhistidine | 0.6 |
| Water, completely desalinated | to 100.000 |

EXAMPLE 3
Hydrogel (polyacrylate gel)

|  | % by weight |
|---|---|
| Acrylic acid polymer (Carbopol 934) | 1.000 |
| Tris(hydroxymethylamino)methane (Tris) | 1.000 |
| Glycerol | 2.000 |
| Propylene glycol | 2.000 |

-continued

|  | % by weight |
|---|---|
| Combination F |  |
| Vitamin E acetate | 3.00 |
| Vitamin A palmitate | 2.60 |
| L-Tryptophan | 2.00 |
| Oleic acid | 0.3 |
| Water, completely desalinated | to 100.000 |

EXAMPLE 4
Formulation of high water content (very soft)

|  | % by weight |
|---|---|
| Ceteareth (Cremophor A 25) | 0.100 |
| Cetearyl alcohol (Lanette O) | 0.400 |
| Vaseline, DAB [German Pharmacopoeia] 9 | 12.500 |
| Mineral oil, DAB 9 | 11.000 |
| Ceteareth 6-stearyl alcohol (Cremophor A6) | 6.000 |
| Combination A: |  |
| Superoxide dismutase | 0.008 |
| Cucumber extract | 2.90 |
| L-methionine | 0.70 |
| Water, completely desalinated | to 100.000 |

EXAMPLE 5
Formulation of high water content (soft)

|  | % by weight |
|---|---|
| Ceteareth 25 (Cremophor A25) | 1.500 |
| Cetearyl alcohol (Lanette O) | 8.500 |
| Combinations A + C |  |
| Catalase | 0.0005 |
| Glutathione peroxidase | 0.0002 |
| Se-methionine | 0.8 |
| Water, completely desalinated | to 100.000 |

EXAMPLE 6
Formulation of high water content (soft)

|  | % by weight |
|---|---|
| Ceteareth 25 (Cremophor A25) | 2.000 |
| Cetearyl alcohol (Lanette O) | 8.000 |
| Vaseline, DAB 9 | 10.000 |
| Mineral oil, DAB 9 | 10.000 |
| Combination D: |  |
| Panthenol | 1.00 |
| Caffeic acid | 0.50 |
| Glutathione peroxidase | 0.002 |
| Water, completely desalinated | to 100.000 |

EXAMPLE 7
Formulation of high water content (moderately firm)

|  | % by weight |
|---|---|
| Ceteareth 25 | 3.000 |
| Cetearyl alcohol (Lanette O) | 17.000 |

-continued

| Combination B | % by weight |
|---|---|
| Glutathione reductase p-isoenzyme | 0.0001 |
| Thiamin pyrophosphate | 0.002 |
| NADPH | 0.004 |
| Coffee extract | 2.95 |
| Water, completely desalinated | to 100.000 |

EXAMPLE 8

Thinly liquid lotion

| | % by weight |
|---|---|
| Ceteareth 25 (Cremophor A25) | 1.000 |
| Ceteareth 6-stearyl alcohol (Cremophor A6) | 1.000 |
| Glycerol monodistearate (Tegin normal) | 2.000 |
| Cetyl alcohol | 1.000 |
| Isopropyl myristate | 1.450 |
| Glycerol | 1.000 |
| Polyvinylpyrrolidone | 0.500 |
| Combination A: | |
| Cholic acid | 0.06 |
| Hamamelis extract | 0.09 |
| Water, completely desalinated | to 100.000 |

EXAMPLE 9

| Viscous lotion | % by weight |
|---|---|
| Ceteareth 25 (Cremophor A25) | 2.000 |
| Cetearyl alcohol (Lanette O) | 3.000 |
| Mineral oil, DAB 9 | 5.000 |
| Propylene glycol | 3.000 |
| Polyvinylpyrrolidone | 0.500 |
| Combination A, B and D | |
| A: | 14.75 |
| B: | 9.52 |
| D: | 12.50 |
| Urea | 4.25 |
| Water, completely desalinated | to100.000 |

EXAMPLE 10

W/O Cream

| | % by weight |
|---|---|
| Glycerol sorbitan fatty acid ester (Arlacel 481) | 6.000 |
| Microcrystalline wax (Lunacera M) | 1.000 |
| Neutral oil | 3.000 |
| Paraffin oil | 19.000 |
| Magnesium stearate | 1.000 |
| Propylene glycol | 3.700 |
| Magnesium sulphate (MgSO$_4$*7H$_2$O) | 0.700 |
| Combination A, B and C | |
| Water, completely desalinated | to 100.000 |

EXAMPLE 11

W/O Emulsion

| | % by weight |
|---|---|
| Polyoxyethylene glycerol sorbitan fatty acid ester (Arlacel 988) | 3.600 |
| Polyoxyethylene fatty acid ester (Arlacel 989) | 1.400 |
| Cetearyl alcohol (Lanette O) | 2.000 |
| Mineral oil, DAB 9 | 20.000 |
| Paraben mixture | as desired |
| Magnesium sulphate (MgSO$_4$*7H$_2$O) | 0.700 |
| Combination A + D + F | |
| CaCl$_2$ | 0.85 |
| Water, completely desalinated | to 100.000 |

EXAMPLE 12

| W/O Lotion | % by weight |
|---|---|
| Glycerol sorbitan fatty acid ester (Arlacel 481) | 1.300 |
| Polyoxyethylene fatty acid ester (Arlacel 989) | 3.700 |
| Neutral oil (Miglyol) | 6.000 |
| Paraffin oil, DAB 9 | 14.000 |
| Propylene glycol | 3.800 |
| Magnesium sulphate (MgSO$_4$*7H$_2$O) | 0.700 |
| Liponic acid | 1.50 |
| Combination A + D | |
| Water, completely desalinated | to 100.000 |

EXAMPLE 13

| O/W Emulsion | % by weight |
|---|---|
| Cetearyl alcohol (Lanette O) | 3.000 |
| Mineral oil, DAB 9 | 25.000 |
| Paraben mixture | as desired |
| Combination C + D | |
| Water, completely desalinated | to 100.000 |

EXAMPLE 14

| O/W Emulsion | % by weight |
|---|---|
| Polysorbate 60 (Tween 60) | 3.000 |
| Sorbitan stearate (Arlacel 60) | 2.000 |
| Cetearyl alcohol (Lanette O) | 3.000 |
| Mineral oil, DAB 9 | 25.000 |
| Paraben mixture | as desired |
| Oleic acid | 0.30 |
| Combination A + E | |
| Water, completely desalinated | to 100.000 |

EXAMPLE 15

Cationic emulsion

| | % by weight |
|---|---|
| Distearyldimethylammonium chloride (Genamin DS AC) | 5.000 |
| Vaseline, DAB 9 | 5.000 |
| Isopropyl palmitate | 2.000 |
| Cetyl alcohol | 1.000 |

-continued

| | % by weight |
|---|---|
| Silicone oil | 0.100 |
| Propylparaben | 0.100 |
| Methylparaben | 0.100 |
| Glycerol | 4.000 |
| Glucose 6-phosphate | 0.50 |
| Combination C + D | |
| Water, completely desalinated | to 100.000 |

EXAMPLE 16

Ionic emulsion

| | % by weight |
|---|---|
| Sodium cetearyl sulphate (Emulgade F) | 6.000 |
| Mineral oil, DAB 9 | 25.000 |
| Paraben mixture | as desired |
| Glucose 1,6-bisphosphate | 2.00 |
| Combination D | |
| Water, completely desalinated | to 100.000 |

EXAMPLE 17

Ionic O/W emulsion

| | % by weight |
|---|---|
| Stearic acid | 5.000 |
| Cetearyl alcohol (Lanette O) | 3.000 |
| Mineral oil, DAB 9 | 25.000 |
| Paraben mixture | as desired |
| Combination C | |
| cis-Urocanic acid | 1.00 |
| Urea | 10.00 |
| Triethanolamine | 1.000 |
| Water, completely desalinated | to 100.000 |

EXAMPLE 18

| Sun oil | % by weight |
|---|---|
| Palmitic acid | 1.00 |
| 3-(4'methylbenzylidine) camphor ("Eusolex 6300", Merck) | 3.00 |
| Myristyl alcohol polyoxypropylated with 3 mol of propylene oxide ("Witconol APM", Witco) | 6.08 |
| $C_{12}$–$C_{15}$-Alcohol benzoate ("Finsolv TN", Witco) | 15.20 |
| Glycerol monococoate, polyoxyethylated with 7 mol of ethylene oxide ("Cetiol HE" Henkel KGaA) | 10.00 |
| Ethanol | 6.50 |
| 2-Octyldodecanol | 12.00 |
| Perfume, correctants, additives, stabilizers | as desired |
| Combination A + D | |
| Water, completely desalinated | to 100.00 |

The constituents of the sun oil are mixed with one another and during this operation, if appropriate, heated to 40 to 50° C. for homogenization.

EXAMPLE 19

| Sun gel | % by weight |
|---|---|
| 2,4,6-Trianilino-(p-carbo-2'-ethylhexyl-1'-oxy)-1,3,5-triazine ("Uvinul" T-150, BASF) | 2.50 |
| Isopropyl myristate | 18.90 |
| $C_{12}$–$C_{15}$-Alcohol benzoate ("Finsolv TN", Witco) | 7.60 |
| Myristyl alcohol, polyoxypropylated with 3 mol of propylene oxide ("Witconol APM", Witco) | 30.40 |
| Caprylic/capric acid triglyceride ("Miglyol neutral oil", Dynamit-Nobel) | 19.50 |
| "Bentone-38", Kronos-Titan | 15.00 |
| Propylene carbonate | 2.00 |
| Ethanol | 2.30 |
| Perfume, correctants, additives, stabilizers | as desired |
| Combination C + D + F | |
| Water, completely desalinated | to 100.00 |

A sun gel is prepared in the customary manner with the constituents mentioned.

EXAMPLE 20

| Hydrogel | % by weight |
|---|---|
| 2-Phenylbenzimidazole-5-sulfonic acid ("Eusolex 232", Merck) | 2.70 |
| Allantoin | 2.0 g |
| Sorbitol, liquid ("Karion F", Merck) | 22.0 |
| "Carbopol 934", B.F. Goodrich | 15.0 |
| Tris(hydroxymethyl)amimomethane | 2.70 |
| Propylene glycol | 10.0 |
| Ethanol | 3.0 |
| Combination B | |
| Perfume, correctants, additives, stablilizers | as desired |
| Water, completely desalinated | to 100.0 |

A hydrogel is prepared in the customary manner with the constituents mentioned.

EXAMPLE 21

| Oil-in-water emulsion (sun cream) | % by weight |
|---|---|
| Combination F | |
| 2-Phenylbenzimidazole-5-sulfonic acid ("Eusolex 232", Merck) | 3.20 |
| Stearyl alcohol oxyethylated with 2 mol of ethylene oxide ("Brij 72", ICI) | 3.00 |
| Stearyl alcohol oxyethylated with 21 mol of ethylene oxide ("Brij 721", ICI) | 3.00 |
| Cetylstearyl alcohol | 12.50 |
| Myristyl alcohol, polyoxypropylated with 3 mol of propylene oxide ("Witconol APM", Witco) | 6.40 |
| $C_{12}$–$C_{15}$-Alcohol benzoate ("Finsolv TN", Witco) | 11.60 |
| Propylene glycol | 8.50 |
| Tris (hydroxymethyl) aminomethane | 1.40 |
| Perfume, correctants, additives, stabilizers | as desired |
| Water, completely desalinated | to 100.0 |

The fatty substances are heated to 80 to 85° C. The water-soluble constituents are dissolved in water at 40° C., the two phases are mixed with one another, while stirring vigorously, and the mixture is allowed to cool, while stirring moderately.

EXAMPLE 22

| Oil-in-water emulsion (sun cream) | % by weight |
|---|---|
| Combination A + B + D | |
| 2,4,6-Trianilino-(p-carbo-2'-ethylhexyl-1'-oxy)-1,3,5-triazine ("Uvinul T-150", BASF) | 1.80 |
| $C_{12}$–$C_{15}$-Alcohol benzoate ("Finsolv TN", Witco) | 4.70 |
| Cetylstearyl alcohol | 3.0 |
| Mixture of stearic acid mono- and diesters of glycerol and stearic acid esters of polyethylene oxide ("Arlacel 165", ICI) | 5.0 |
| Myristyl alcohol, polyoxypropylated with 3 mol of propylene oxide ("Witconol APM", Witco) | 18.5 |
| Perfume, correctants, additives, stabilizers | as desired |
| Water, completely desalinated | to 100.0 |

The emulsion is prepared in accordance with the above example.

EXAMPLE 23

| Water-in-oil emulsion (sunscreen milk) | % by weight |
|---|---|
| Combination C + F | |
| 1-(4'-tert-Butylphenyl)-3-(4'-methoxyphenol)propane-1,3-dione ("Parsol 1789", Givaudan) | 1.50 |
| 2'-Ethylhexyl 4-methoxycinnamate ("Parsol MCX", Givaudan) | 3.50 |
| Esters of saturated fatty acids with polyethylene oxide ("Arlacel 989", ICI) | 3.70 |
| Esters of unsaturated fatty acids with glycerol and sorbitan ("Arlacel 481", ICI) | |
| Myristyl alcohol, polyoxypropylated with 3 mol of propylene oxide ("Witconol APM", Witco) | 16.00 |
| $C_{12}$–$C_{15}$-Alcohol benzoate (37 Finsolv TN", Witco) | 4.00 |
| Magnesium sulphate heptahydrate | 0.70 |
| Perfume, correctants, additives, stabilizers | as desired |
| Water, completely desalinated | to 100.0 |

The emulsion is prepared in a manner corresponding to that described under Example 21.

EXAMPLE 24

| Water-in-oil emulsion (sunscreen milk) | % by weight |
|---|---|
| Combination A + C | |
| 2'-Ethylhexyl 4-methoxycinnamate ("Parasol MCX", Givaudan) | 1.50 |
| 3-(4'-Methylbenzylidene)camphor ("Eusolex 6300", Merck) | 3.0 |
| Esters of unsaturated fatty acids with glycerol and sorbitan ("Arlacel 481", ICI) | 6.00 |
| | 1.00 |
| Microwax ("Lunacera 11", Fuller) | 2.00 |
| Caprylic/capric acid triglyceride ("Miglyol neutral oil", Dynamit-Nobel) | |
| Myristyl alcohol, polyoxypropylated with 3 mol of propylene oxide ("Witconol APM", Witco) | 1.45 |
| $C_{12}$–$C_{15}$-Alcohol benzoate ("Finsolv TN", (Witco) | 3.70 |
| Magnesium stearate | 1.00 |
| Propylene glycol | 3.70 |
| Magnesium heptahydrate | 0.70 |
| Perfume, correctants, additives, stabilizers | as desired |
| Water, completely desalinated | to 100.0 |

The emulsion is prepared in a manner corresponding to that described under Example 21.

EXAMPLE 25

| Water-in-oil emulsion (sunscreen milk) | % by weight |
|---|---|
| $FADH_2$ | 0.09 |
| Glucose 1,6-phosphate | 1.23 |
| D-Biotin | 0.04 |
| D-Carnosine | 1.0 |
| Vitamin C dipalmitate | 2.0 |
| Vitamin E acetate | 3.0 |
| Phytic acid | 1.70 |
| Urocanic acid | 1.30 |
| L-Cysteine | 1.57 |
| Dithiopropyl gallate | 4.00 |
| 2'-Ethylhexyl 4-methoxycinnamate ("Parsol MCX", Givaudan) | 1.50 |
| 3-(4'Methylbenzylidene)camphor ("Eusolex 6300", Merck) | 3.0 |
| Esters of unsaturated fatty acids with glycerol and sorbitan ("Ariacel 481", ICI) | 6.00 |
| Microwax ("Lunacera 11", Fuller) | 1.00 |
| Caprylic/capric acid triglyceride ("Miglyol neutral oil", Dynamit-Nobel) | 2.0 |
| Myristyl alcohol, polyoxypropylated with 3 mol of propylene oxide ("Witconol APM", Witco) | 119.0 |
| $C_{12}$–$C_{15}$-Alcohol benzoate ("Finsolv TN", Witco) | 30.0 |
| Magnesium stearate | 1.00 |
| Propylene glycol | 3.70 |
| Magnesium sulphate heptahydrate | 7.0 |
| Perfume, correctants, additives, stabilizers | as desired |
| Water, completely desalinated | to 100.0 |

The emulsion is prepared in the same manner as in Example 21.

EXAMPLE 26

| Cationic emulsion for rinsing the hair | % by weight |
|---|---|
| Vitamin E acetate | 16.5 |
| trans-Urocanic acid | 7.0 |
| Dimethyldistearylammonium chloride ("Arosorf TA 100", Rewo) | 5.00 |
| Vaseline | 5.00 |
| Isopropyl palmitate | 2.0 |
| Cetyl alcohol | 10.0 |
| Water | 8.33 |
| Glycerol | 4.0 |
| Perfume, correctants, additives, stabilizers | as desired |
| Water, completely desalinated | to 100.0 |

A hair rinse is prepared in the customary manner using the constituents mentioned.

To prepare the topical preparations, the active compounds and active compound combinations are dissolved in the aqueous phase or in the fatty phase and further processed in a known manner.

Preparation of Capsules

Capsules which comprise the constituents stated below are prepared by known working procedures. These are suitable for treatment of the abovementioned diseases in dosage amounts of in each case one capsule once or several times daily.

EXAMPLE 27

| Constituents | % by weight |
|---|---|
| Vitamin E palmitate | 5.0 |
| Ca ascorbyl phosphate | 5.0 |
| DL-Carnosine | 2.5 |
| Combination A | |
| Combination D | |

We claim:

1. A method for the treatment or for the prophylactic treatment of hyperreactive skin predisposed to dermatitis, deficient, hypoactive skin or dermatoses which comprise applying to said skin an effective amount of a composition comprising one or more flavonoids.

2. The method according to claim 1, wherein the flavonoid in the composition is selected from the group consisting of quercitin, rutin, chrysin, kaempferol, myricetin, rhamnetin, apigenin, luteolin, naringin, hesperidin, naringenin, hesperitin, morin, phloridzin, diosmin, fisetin, vitexin, neo-hesperidin dihydrochalcone, flavone, glucosylrutin and genistein, alpha-glucosylrutin, alpha-glucosylmyrictrin, alpha-glucosylisoquercitrinitrin and alpha-glucosylquercitrin, alpha-glucosylmyrictrin, alpha-glucosylisoquercitrinitrin and alpha-glucosylquercitrin.

3. The method according to claim 1, wherein the flavonoid in the composition is alpha-glucosylrutin.

4. The composition of claim 1, further comprising one or more compounds selected from the group consisting of an antioxidant;

an endogenous energy metabolism metabolide;

an endogenous enzymatic antioxidant system or a synthetic derivative thereof (mimics);

an antimicrobial action system;

an antiviral action system.

* * * * *